(12) United States Patent
Petersen et al.

(10) Patent No.: US 12,644,090 B2
(45) Date of Patent: Jun. 2, 2026

(54) SYSTEMS AND METHODS FOR TISSUE EVALUATION

(71) Applicant: United Therapeutics Corporation, Silver Spring, MD (US)

(72) Inventors: Thomas Petersen, Durham, NC (US); Jeffrey Soohoo, Chapel Hill, NC (US); Blair Dodson, Durham, NC (US); Joseph Papu, Raleigh, NC (US); Joanna Peterschmitt, London (GB)

(73) Assignee: United Therapeutics Corporation, Silver Spring, MD (US)

( * ) Notice: Subject to any disclaimer, the term of this patent is extended or adjusted under 35 U.S.C. 154(b) by 826 days.

(21) Appl. No.: 17/943,728

(22) Filed: Sep. 13, 2022

(65) Prior Publication Data

US 2023/0079079 A1    Mar. 16, 2023

Related U.S. Application Data

(60) Provisional application No. 63/243,929, filed on Sep. 14, 2021.

(51) Int. Cl.
| | |
|---|---|
| *C12M 1/34* | (2006.01) |
| *C12M 1/00* | (2006.01) |
| *C12M 1/12* | (2006.01) |
| *C12M 1/36* | (2006.01) |
| *C12M 1/42* | (2006.01) |
| *C12M 3/00* | (2006.01) |

(52) U.S. Cl.
CPC ............ *C12M 41/46* (2013.01); *C12M 21/08* (2013.01); *C12M 25/14* (2013.01); *C12M 29/10* (2013.01);
(Continued)

(58) Field of Classification Search
CPC .... A61M 5/1723; C12M 21/08; C12M 25/10; C12M 25/14; C12M 29/10; C12M 35/04;
(Continued)

(56) References Cited

U.S. PATENT DOCUMENTS

| | | | |
|---|---|---|---|
| 2006/0089592 A1* | 4/2006 | Kadhiresan | ............ G16H 20/13 128/923 |
| 2012/0123229 A1 | 5/2012 | Butterfield et al. | |

(Continued)

FOREIGN PATENT DOCUMENTS

| | | |
|---|---|---|
| EP | 3 375 364 A1 | 9/2018 |

OTHER PUBLICATIONS

Westerhof, Nico, Jan-Willem Lankhaaar, Berend E. Westerhof. "The arterial Windkessel" Med Bio Eng Comput (2009) 47:131-141. (Year: 2009).*

(Continued)

*Primary Examiner* — Michael L Hobbs
(74) *Attorney, Agent, or Firm* — Foley & Lardner LLP

(57) ABSTRACT

A system includes one or more processors configured to receive a signal indicative of at least one of a flow or a pressure through a tissue; apply the signal as an input to a model comprising an airway component corresponding to an airway of the tissue, a vascular component corresponding to at least one of an artery or a vein of the tissue, and a barrier component between the airway component and the vascular component; and generate, responsive to applying the signal to the model, an evaluation score indicative of a quality of the tissue.

15 Claims, 11 Drawing Sheets

(52) U.S. Cl.
    CPC ............ *C12M 35/04* (2013.01); *C12M 41/40*
        (2013.01); *C12M 41/48* (2013.01)

(58) Field of Classification Search
    CPC ...... C12M 41/40; C12M 41/46; C12M 41/48;
        G16H 50/50
    USPC ...................................................... 435/284.1
    See application file for complete search history.

(56) References Cited

U.S. PATENT DOCUMENTS

2015/0289501 A1* 10/2015 Raredon ................ A61K 35/42
                                                  435/284.1
2017/0281278 A1* 10/2017 Higaki ................... A61B 6/504

OTHER PUBLICATIONS

Chemla et al. "Pulmonary vascular resistance and compliance relationship in pulmonary hypertension," European Respiratory Journal, 2015, 46(4):1178-1189.

Engler et al., "Non-invasive and real-time measurement of microvascular barrier in intact lungs," Biomaterials, Oct. 2019, 217:119313, 1-12.

Petak et al., "Effects of pulmonary vascular pressures and flow on airway and parenchymal mechanics in isolated rat lungs," Journal of Applied Physiology , 2002, 92(1):169-178.

Saouti et al. "The arterial load in pulmonary hypertension," European Respiratory Review, 2010, 19(117):197-203.

Thenappan et al. "The critical role of pulmonary arterial compliance in pulmonary hypertension," Annals of the American Thoracic Society, Feb. 2016, 13(2):276-284.

* cited by examiner

Airway (AW)
$R_{aw}$: Resistance of airway
$C_{aw}$: Compliance of airway
Barrier (Leak between Airway-Vascular)
$R_b$: Resistance of barrier
$C_b$: Compliance of barrier
Pulmonary Arterial (PA)-Venous (PV)
$R_{pa}$: Resistance of pulmonary arteries
$R_{pv}$: Resistance of pulmonary veins
$C_{pv}$: Compliance of pulmonary veins

SYSTEMS AND METHODS FOR TISSUE EVALUATION

CROSS-REFERENCE TO RELATED APPLICATIONS

The present application claims the benefit of and priority to U.S. Provisional Application No. 63/243,929, filed Sep. 14, 2021, the disclosure of which is incorporated herein by reference in its entirety.

TECHNICAL FIELD

The present application relates to a method of evaluating tissue using a flow model that assesses resistance and compliance of tissue.

BACKGROUND

Engler et al. (Biomaterials, 2019 October; 217: 119313) discloses a model that allows direct, non-invasive measurement of average alveolar and capillary pressures, tracks flow paths within the organ, and enables calculation of lumped internal resistances including microvascular barrier.

A need exists for methods of non-invasively evaluating tissue that allow a more accurate understanding of natural or artificial tissues used for transplantation and development of improved organs or organ-like material.

SUMMARY

One embodiment is a method of evaluating a tissue. The method can include receiving, by one or more processors, a signal indicative of at least one of a flow or a pressure through the tissue; applying, by the one or more processors, the signal as an input to a model including an airway component, a vascular component, and a barrier component between the airway component and the vascular component; and generating, by the one or more processors responsive to applying the signal to the model, an evaluation score indicative of a quality of the tissue.

Another embodiment is a system. The system can include one or more processors configured to receive a signal indicative of at least one of a flow or a pressure through the tissue; apply the signal as an input to a model including an airway component corresponding to an airway of the tissue, a vascular component corresponding to at least one of an artery or a vein of the tissue, and a barrier component between the airway component and the vascular component; and generate, responsive to applying the signal to the model, an evaluation score indicative of a quality of the tissue.

DETAILED DESCRIPTION

Unless otherwise specified, "a" or "an" means "one or more."

The present invention is further illustrated by, though in no way limited to, the following examples.

Tissue transplantation requires a biologic product, either from a human donor or produced with engineered tissue, to meet certain physiological standards. A lumped parameter model according to an embodiment satisfies a need to determine minimum perfusion requirements for a native and/or engineered tissue for transplantation. Lumped parameter models are a tool traditionally used to measure clinical disease. The inventors are not aware of lumped parameter models being used to track and qualify tissues for human transplantation.

The systems and method of the present application can be used for any perfusable soft tissue materials, native or engineered. Optionally, material can be native tissues such as arteries, veins, kidneys, livers, skeletal muscle, and the like. Alternatively, the material may include hydrogels, polytetrafluoroethylene (PTFE), or other hyperelastic, soft perfusable materials.

Figure 1:
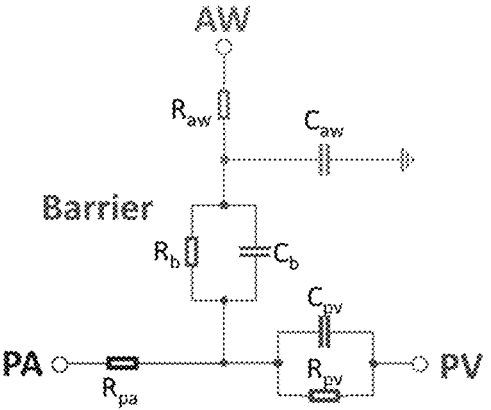
FIG. 1 shows a lumped parameter lung model for evaluating a tissue to be tested that includes both resistance and capacitance.

An embodiment is a system for qualification of a tissue to be used in tissue transplantation, comprising a model, a signal, and computational analysis to test system function using a lumped parameter approach for evaluating the tissue. The tissue can be a tissue scaffold (e.g,. made of various natural or manufactured materials), engineered tissue (e.g., a tissue having had any of various processes applied), or native tissue. FIG. 1 represents a total lung model for evaluating a native or engineered tissue. The model can be a 3-element Windkessel model. The model can include a lung circuit connecting the airway and the vasculature of the tissue. The model can be used to monitor and evaluate engineered tissues in culture, or a native tissue assessment, including before transplant.

The model includes both a resistance component for measuring a tissue's resistance and a capacitive element to represent tissue compliance (e.g., the compliance representing physiological and/or material properties of the tissue). This provides an in-process measurement that is directly comparable with ventilator compliance and a measure of vascular compliance that clinically has been shown to be prognostic indicator of lung health status. In pulmonary hypertension, models have been used to track disease progression of vascular changes in pulmonary vascular resistance, compliance and impedance also known as right ventricle after load. [Saouti, N., et al. "The arterial load in pulmonary hypertension." European Respiratory Review 19.117 (2010): 197-203.]; [Thenappan, Thenappan, et al. "The critical role of pulmonary arterial compliance in pulmonary hypertension." Annals of the American Thoracic Society 13.2 (2016): 276-284.]; [Chemla, Denis, et al. "Pulmonary vascular resistance and compliance relationship in pulmonary hypertension." European Respiratory Journal 46.4 (2015): 1178-1189.] In addition to vascular resistance and compliance changes, the airway has increased resistance in experimental animal models of pulmonary hypertension with disease progression. [Petak, Ferenc, et al. "Effects of pulmonary vascular pressures and flow on airway and parenchymal mechanics in isolated rat lungs." Journal of applied physiology 92.1 (2002): 169-178.] The model can be used to test both native and engineered lungs, for example, for vascular and airway function as described in more detail below. While the model is preferably used with a lung tissue, it may be applied to any tissue or material, native or engineered, that experiences a pressure and flow.

Figure 2:
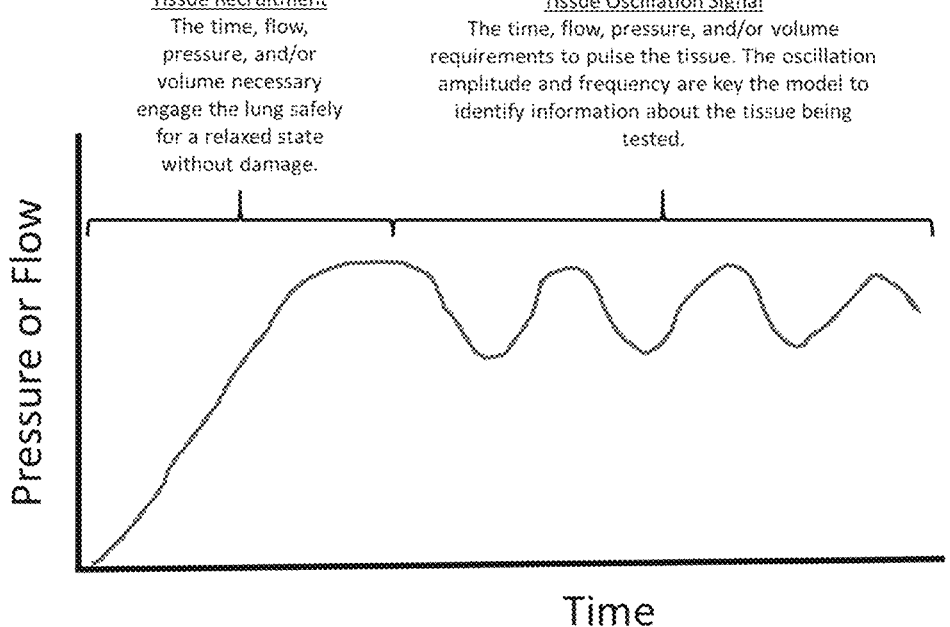
FIG. 2 shows an input signal useful in a model of FIG. 1 by determining optimal flows and/or pressures for testing a tissue. The signal developed was in ex vivo lung perfusion (EVLP) and in a bioreactor with tissue pre-recruited from a static state due to its visco-elastic nature. The tissue is tested cyclically to determine the physiologic parameters.

An embodiment relates to a method for measuring tissue quality of a lung or tissue to be used for a lung transplant. The method is a minimally invasive approach to test tissues in both ex vivo lung perfusion system and in a bioreactor in which an engineered tissue is being produced. An input signal for the evaluation method involves several steps as shown in FIG. 2. The method preferably utilizes a set of flows and/or pressures for testing a tissue. For example, in the engineered lung, initial settings for airway flows can be between 60-150 ml/min, pressures below 15 mmHg, and volume ranges between 300-600 ml, ELN entry "RLAN-20200204A: STR . . . Magnitude Summary". The initial ranges the vasculature in the tissue engineered lung are flows between 60-150 ml/min and pressures below 20 mmHg, ELN entry "RLAN-20200220A: STR . . . Magnitude Study". Various such settings can be scaled based on a size metric of the tissue (e.g., the settings provided above are for a 120 g lung, which is about one half to one third of the size of a human lung, and thus can be scaled based on the size metric of the human lung relative to the settings, such as based on a ratio of masses). The signal developed was in ex vivo lung perfusion (EVLP) and in a bioreactor. The tissue is pre-recruited from a static state due to the viscoelastic nature of tissue. The tissue is then tested cyclically to determine physiologic parameters.

Figure 3:
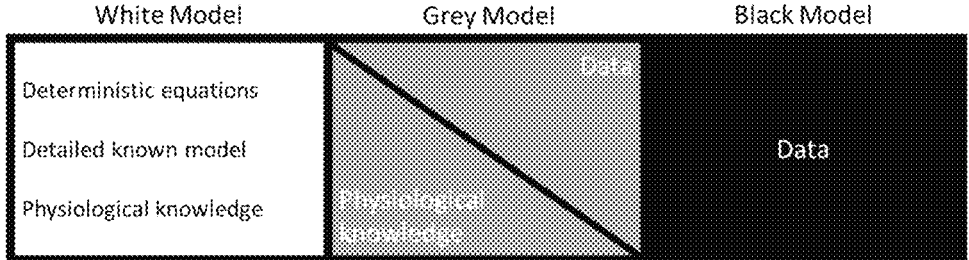
FIG. 3 shows a summary of a grey model that leverages deterministic equations about soft tissue physiology with data collected during a tissue perfusion process. The data can be fitted to the series of equations to determine tissue quality during the perfusion process prior to a transplant.

An embodiment includes a computational approach to measure model elements and relate them to physiological parameters. The signal is entered into a computational model to determine physiological element measures for tissue function as follows. A program was created in Matlab to solve a system of differential equations for fluids in a soft tissue using a Grey Model approach to relate the collected data during the external perfusion, as showing in FIG. 3. The model leverages deterministic equations about soft tissue physiology with data collected during a benchmark perfusion process. The data can include input data and output data from the perfusion process, which can be fit to the series of equations to determine tissue quality during the perfusion process prior to transplant.

Another embodiment generates rapid calculations for modeling pressure and flow relationships in lung or other tissues. The invention can be used to measure perfusion integrity of native tissues that may include vascular grafts, kidneys, livers, lungs, or any tissue that has fluid (either liquid or gas) perfusion.

The present invention is further illustrated by, though in no way limited to, the following examples.

Example 1

Figure 4:
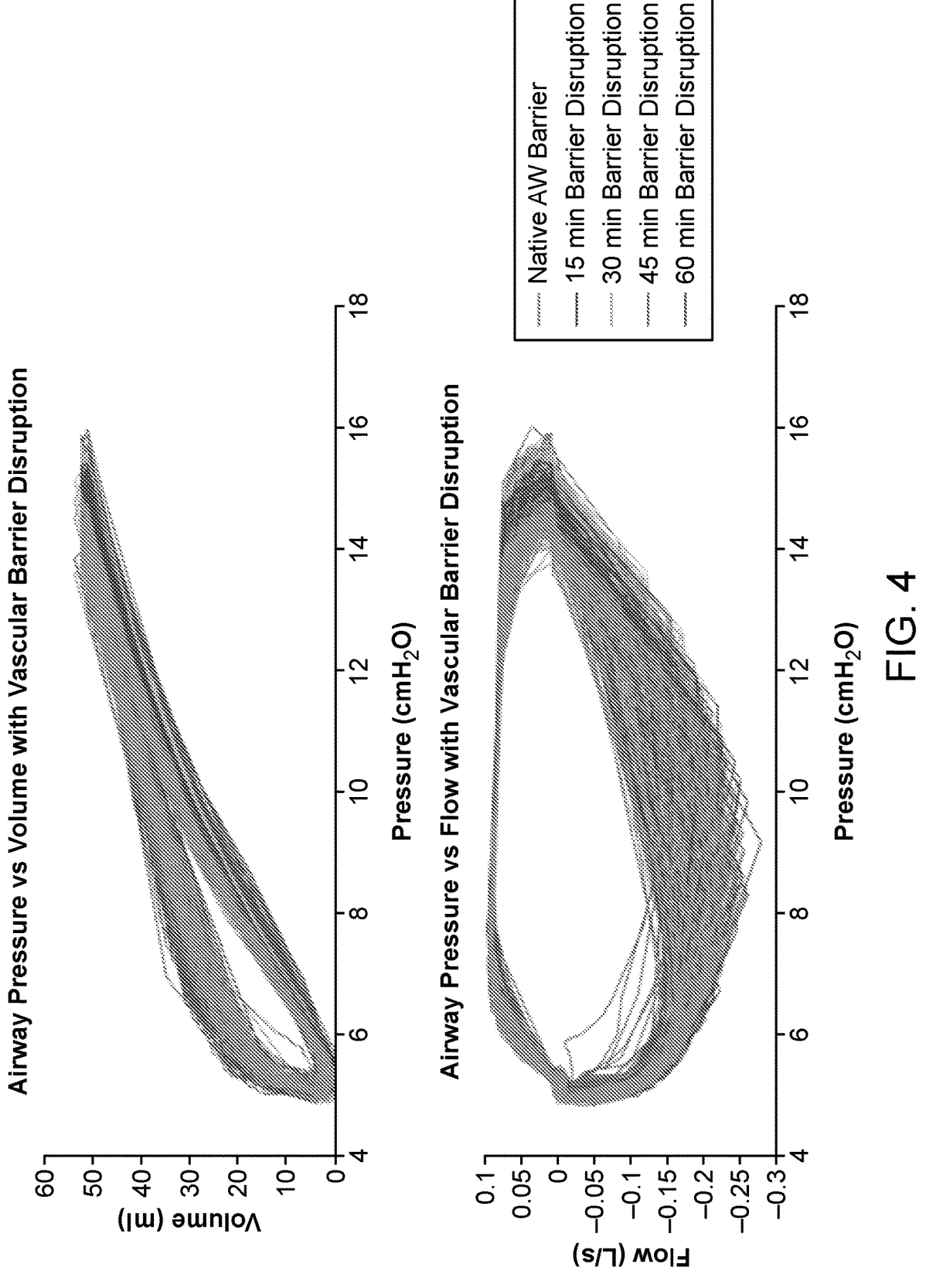
FIG. 4 shows disruption of the airway-vascular barrier by injection of 0.2% Triton into the vasculature, which slowly erodes the airway barrier. The airway perfusion shifts to higher pressure and lower volumes and flows. An embodiment permits evaluation of the changes in perfused organs with such treatments.

Measurements were developed for native tissue prior to transplant using in vitro pulsatile tests and making use of the lumped parameter model described above. These tests were done in native pig lungs to demonstrate the following:

(A) characterize the airway barrier integrity—The airway barrier during air perfusion in native lungs has a steady pressure, flow, and volume profile. When the airway barrier is compromised with a vascular antagonist and fluid crosses into the airway, pressures increase with reduced flows and volumes as shown in FIG. 4. The model allows for determining the degree of airway barrier integrity and treatment with in-process therapies to improve an area of damaged or substandard quality tissue.

Figure 5:
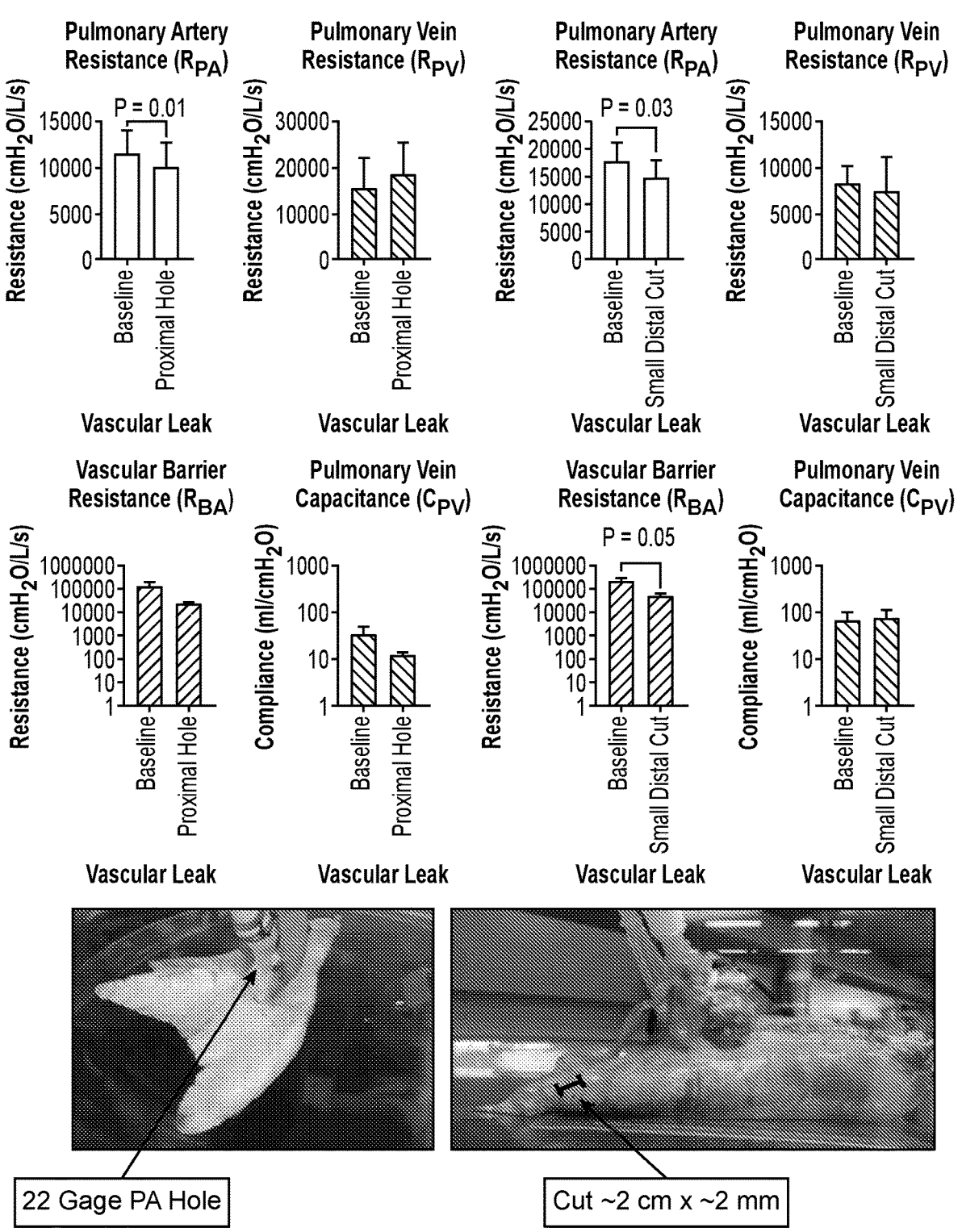
FIG. 5 shows an embodiment for evaluating a leak by making a cut in the distal lung that reduces the pulmonary artery and the vascular barrier resistances.

(B) determine a proximal vs distal vascular leak—Modeling allows us to locate a leak through creating separate elements as shown in FIG. 5. A proximal hole significantly reduces resistance in the pulmonary artery. However, a leak more distal in the lung is characterized by decreased pulmonary artery and barrier resistances. This is important in determining the barrier status by continuous monitoring across the arterial, venous, and barrier model elements of the lung. A model can be customized to an organ system to determine leak through different elements in the system where flow and pressure are tracked. The vascular leak can be monitored and treated with in-process therapies. A 22-gage hole in the proximal pulmonary artery (PA) reduces resistance. A cut in the distal lung reduces the pulmonary artery and the vascular barrier resistances. A model allows components of an organ to be monitored for changes during ex vivo perfusion.

Figure 6:
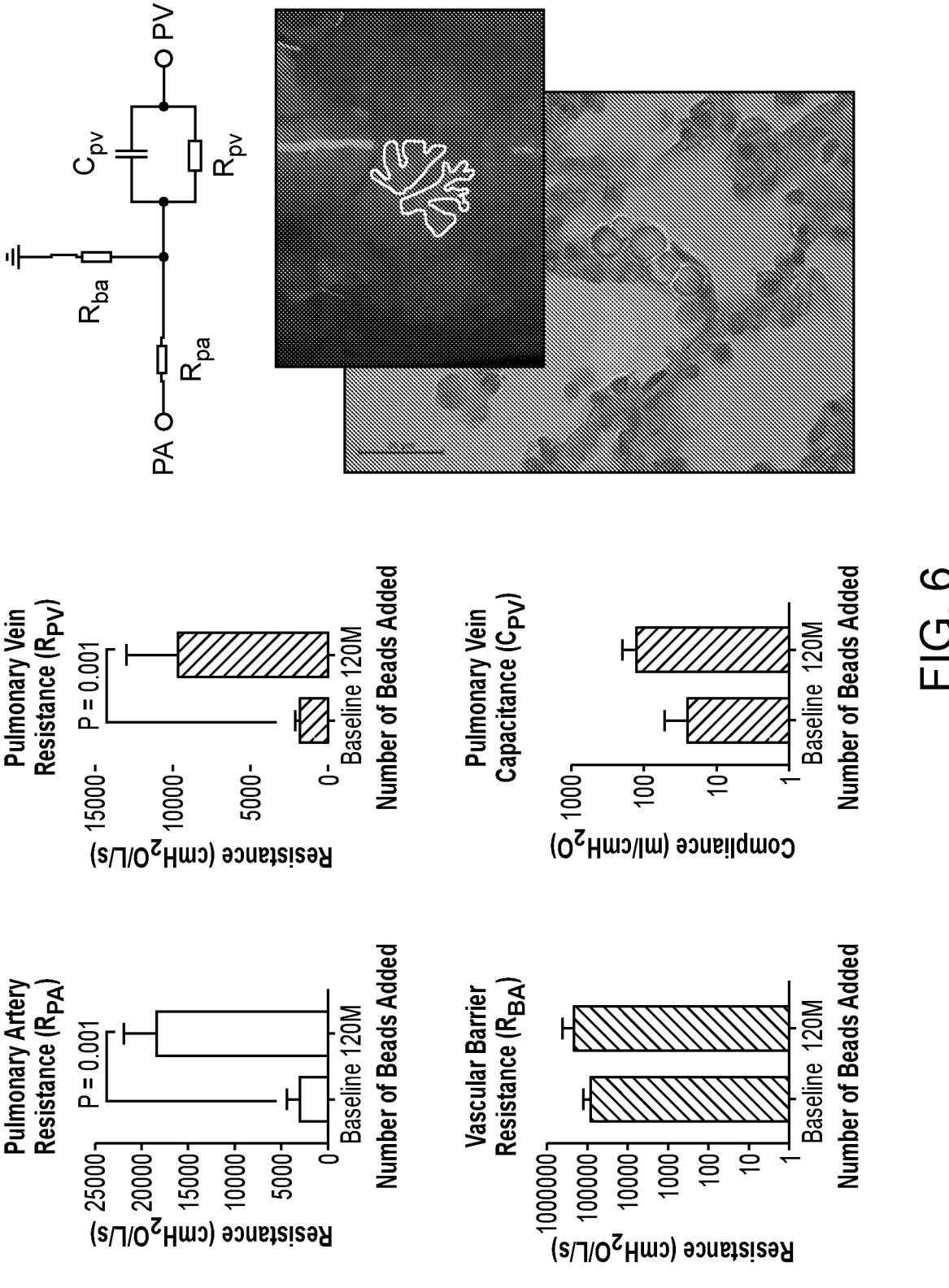
FIG. 6 shows an embodiment for evaluating the occlusion of vessels and progression by monitoring increases in pulmonary artery (PA) and pulmonary vein (PV) resistances.

(D) determine the patency of capillaries—Clogging capillaries alters the model by increasing arterial and venous resistance components to flow simulated by injecting beads into a lung, figure. Organs perfused with blood, may be subject to blockage. This would allow monitoring of the blockage of flow within an organ as shown in FIG. 6. Using a lung model, the occlusion of vessels and progression is tracked by monitoring increases in pulmonary artery (PA) and pulmonary vein (PV) resistances. Modeling allows tracking of vessel patency during ex vivo perfusion.

Figure 7:
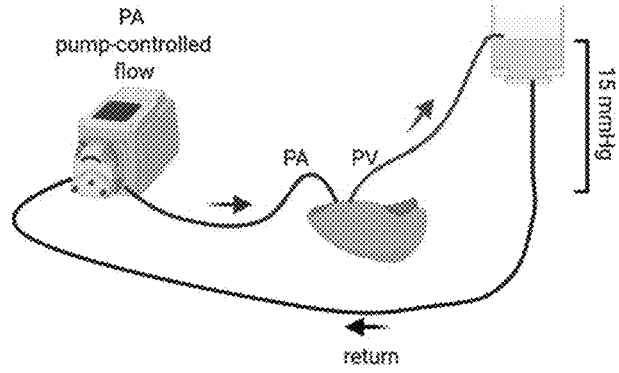
FIG. 7 shows an arrangement of components in an embodiment of the invention showing relationship between a perfusion device and an organ being modeled to determine the interaction.

(E) define the interaction between an organ and the perfusion setup—In-process modeling can be used to tune lung-system interactions for achieving and implementing specific design objectives, including testing and optimizing pumps, fluid reservoir level, pressure limits, sensor configuration, and sensor resolution based upon organ modeling, as shown in FIG. 7.

Interaction between the perfusion device and the organ is modeled to determine the interaction. Pump setup and reservoir pressures are optimized based upon the modeling parameters.

Example 2

Figure 8:
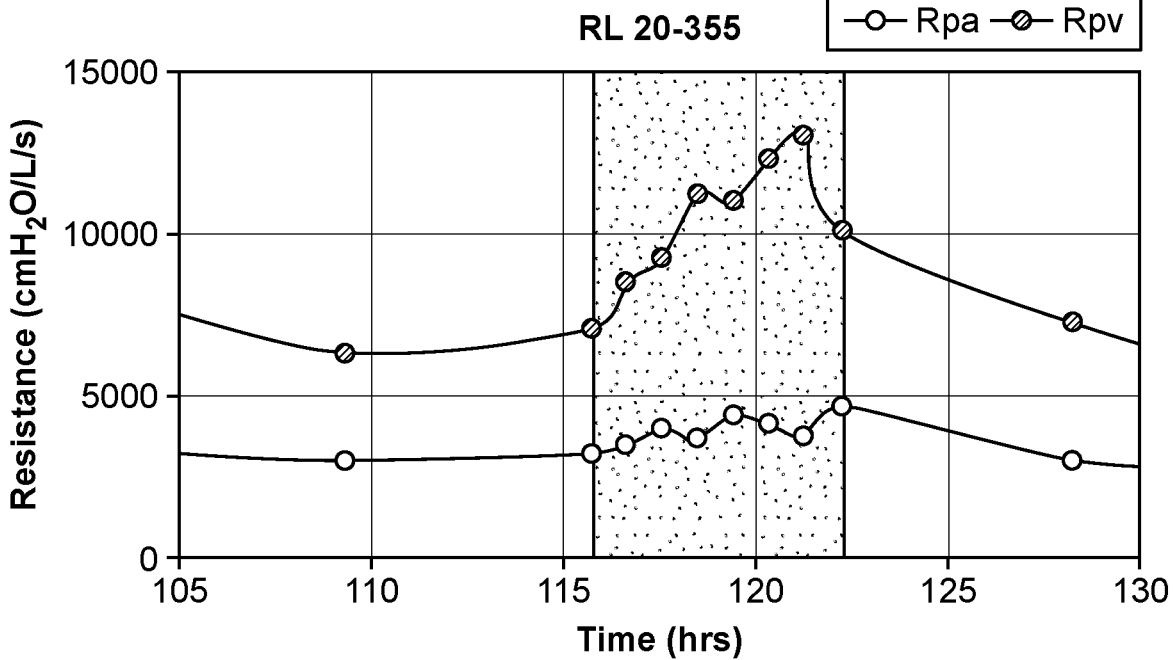
FIG. 8 shows results of an experiment in which cells were added and modeling was used to determine lung resistance during the process of adding cells to a lung scaffold, which allows instant feedback on vessel patency based upon the addition of cells.

For engineered tissue, the model can be applied for several important and unique uses, which include:

(A) The ability to tune cell seeding—In-process testing and modeling simulations allow seeding tuning to hit limits of vessel occlusion based upon model components. FIG. 8 shows results of an experiment in which cells were added and modeling was used to determine lung resistance during the process of adding cells to a lung scaffold. The modeling approach allows instant feedback on vessel patency based upon the addition of cells, allowing a unique seeding process to be controlled with the model.

(B) Evaluate manufacturing process—Modeling allows a way to compare tissue properties during the engineering process. Modeling is used to evaluate lungs during the decellularization process, from an initial porcine lung to a decellularized extracellular matrix scaffold. The storage of the scaffold and transition to the recellularization process can be assessed with modeling of the perfusion process.

Figure 9:
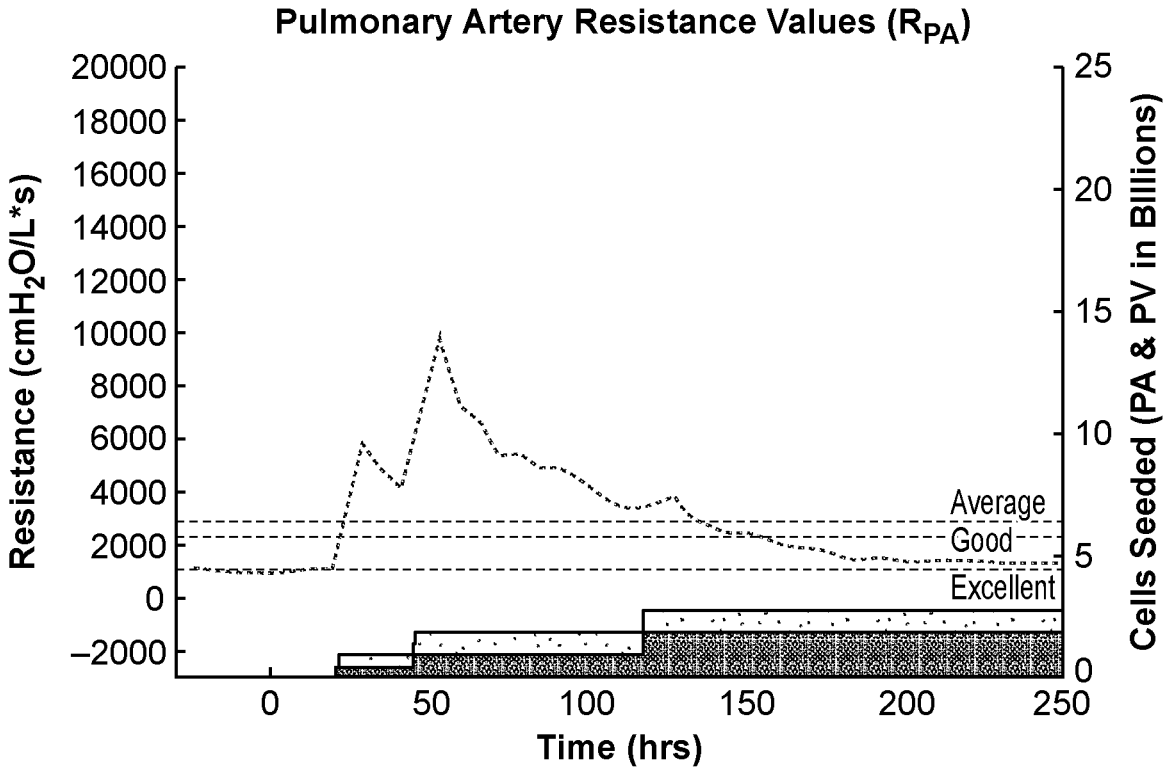
FIG. 9 shows an example of cell seeding in the PA (in blue) and PV (in red) where pulmonary artery resistance changes are monitored in the engineered lung to determine culture time in between and after seedings.

(C) Monitoring of culture time with proposed benchmarks—Determining targets of pulmonary vascular resistance to set the length of culture of a tissue. FIG. 9 provides an example of cell seeding in the PA (in blue) and PV (in red) monitoring pulmonary artery resistance changes in the engineered lung to determine culture time in between and after seedings.

Figure 10:
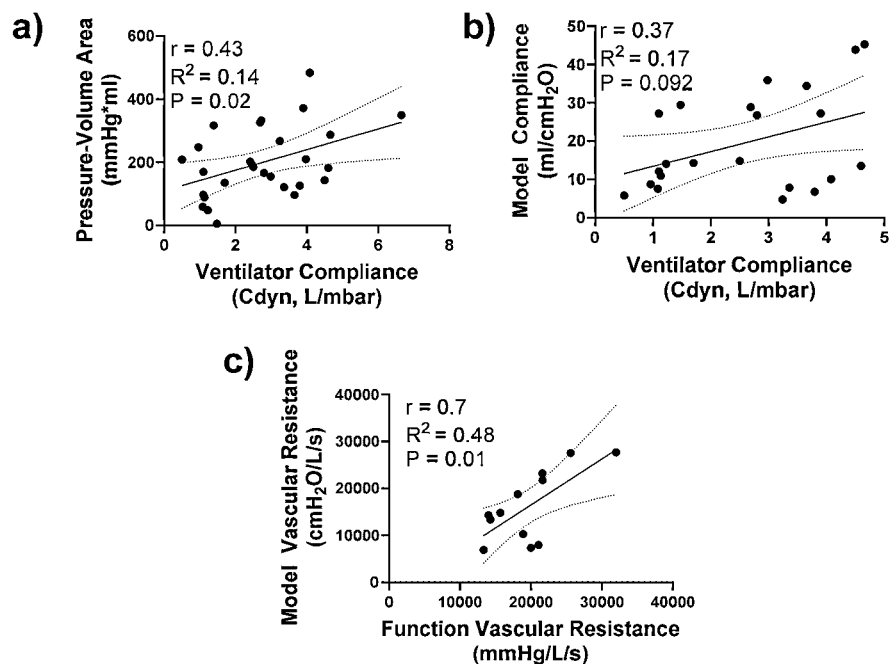
FIG. 10 shows relationship between in-process metrics and their ex vivo perfusion equivalent for function.

(D) Measurements of functional outcomes—In-process metrics can be related to standard ex vivo lung perfusion metrics. FIG. 10 shows relationship between in-process metrics and their ex vivo perfusion equivalents for function.

Figure 11:
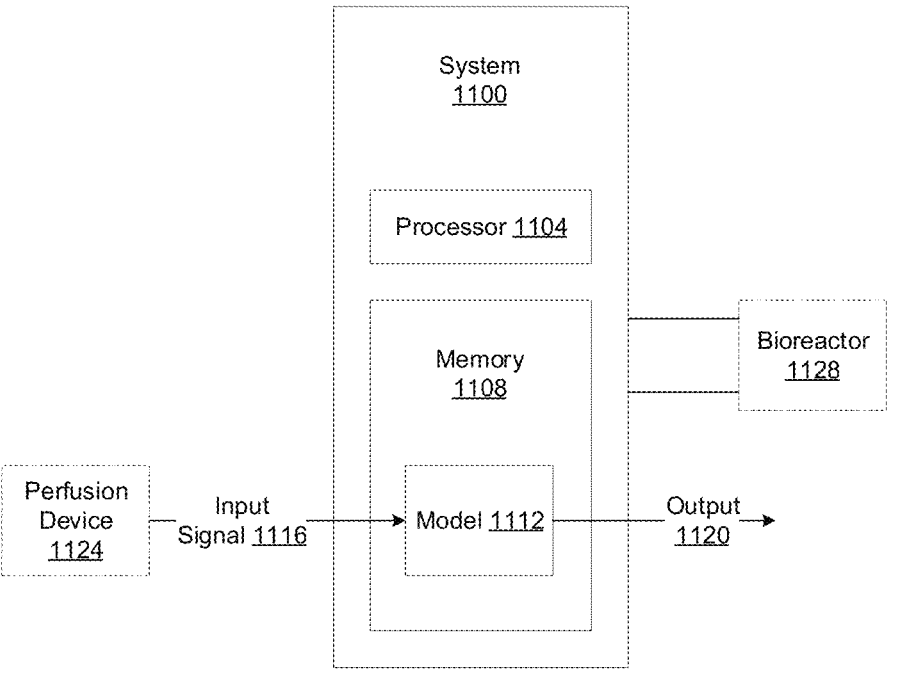
FIG. 11 shows an example of a system determining an evaluation score of a tissue.

FIG. 11 shows an example of a system 1100 that can be used to determine an evaluation score of a tissue. The system 1100 can incorporate features of and be used to implement various examples of the modeling described herein, including using a lumped parameter model to determine the evaluation score for the tissue based on the tissue's resistance and compliance. The system 1100 can include or be communicably coupled with at least one of a perfusion device (e.g., to apply fluid flow to the tissue in order to monitor flow data regarding the tissue) or a bioreactor (e.g., to monitor and control generation of engineered tissue responsive to the evaluation score).

The system 1100 can include one or more processors 1104 and memory 1108 (which can be implemented using one or more processing circuits). The processors 1104 and memory 1108 can include various components including graphics processing units (GPUs) and parallel computing components. The processor 1104 may be a general purpose or specific purpose processor, an application specific integrated circuit (ASIC), one or more field programmable gate arrays (FPGAs), a group of processing components, or other suitable processing components. The processor 1104 may be configured to execute computer code or instructions stored in memory 1108 (e.g., fuzzy logic, etc.) or received from other computer readable media (e.g., CDROM, network storage, a remote server, etc.) to perform one or more of the processes described herein. The memory 1108 may include one or more data storage devices (e.g., memory units, memory devices, computer-readable storage media, etc.) configured to store data, computer code, executable instructions, or other forms of computer-readable information. The memory 1108 may include random access memory (RAM), read-only memory (ROM), hard drive storage, temporary storage, non-volatile memory, flash memory, optical memory, or any other suitable memory for storing software objects and/or computer instructions. The memory 1108 may include database components, object code components, script components, or any other type of information structure for supporting the various activities and information structures described in the present disclosure. The memory 1108 may be communicably connected to the processor 1104 and may include computer code for executing one or more of the processes described herein. The memory 1108 can include various modules (e.g., circuits, engines) for completing processes described herein. The system 1100 can include wired or wireless communications electronics to communicate with other devices, such as remote databases.

The system 1100 can include a model 1112. The model 1112 can incorporate features of the model described with respect to FIG. 1. For example, the model 1112 can be a Windkessel model that includes resistance parameters corresponding to flow resistance through the tissue and capacitance parameters corresponding to flow compliance through the tissue. For example, the model 1112 can include an airway component including an airway resistance parameter of an airway of the tissue and an airway compliance parameter of the airway; a barrier component including a barrier resistance parameter and a barrier compliance parameter; and a vascular (e.g., components representing one or more arteries, arterioles, capillaries, veins, venules, or a network thereof) component including parameters such as a pulmonary artery resistance parameter (which can include or be based on resistances of arteries or arterioles downstream of the pulmonary artery), a pulmonary vein resistance parameter (which can include or be based on resistances of veins or venules upstream of the pulmonary vein), and a pulmonary vein compliance parameter (which can include or be based on resistances of veins or venules upstream of the pulmonary vein).

An input signal 1116 can be applied to the model 1112 to cause the model to generate an output 1120, such as an evaluation score representing an evaluation of flow through the tissue. The model 1112 can be evaluated. The input signal 1116 can incorporate features of the signal described with respect to FIG. 2. For example, the input signal 1116 can be a tissue oscillation signal. The system 1100 can include or be coupled with a perfusion device 1124, which can perform a perfusion operation on the tissue and detect the input signal 1116 to provide the input signal 1116 to the one or more processors 1104.

The system 1100 can include or be coupled with a bioreactor 1128 that generates the tissue (e.g., generates engineered tissue). The one or more processors 1108 can control operation of the bioreactor 1128 responsive to the evaluation score. For example, the one or more processors 108 can cause the bioreactor 1128 to adjust a culture time of the tissue responsive to the evaluation score.

All references disclosed herein are specifically incorporated by reference thereto.

While preferred embodiments have been illustrated and described, it should be understood that changes and modifications can be made therein in accordance with ordinary skill in the art without departing from the invention in its broader aspects as defined herein.

What is claimed is:

1. A method of evaluating a tissue, comprising:

receiving, by one or more processors, a signal indicative of at least one of flow or pressure through the tissue, the tissue comprising at least one of a tissue scaffold, an engineered tissue, or a native tissue;

applying, by the one or more processors, the signal as an input to a model comprising an airway component, a vascular component, and a barrier component between the airway component and the vascular component; and generating, by the one or more processors responsive to applying the signal to the model, at least one of an integrity of an airway barrier corresponding to the barrier component, a leak of the tissue, or a patency of one or more vessels of the tissue.

2. The method of claim 1, wherein the airway component comprises an airway resistance parameter and an airway compliance parameter, the barrier component comprises a barrier resistance parameter and a barrier compliance parameter, and the vascular component comprises a pulmonary artery resistance parameter, a pulmonary vein resistance parameter, and a pulmonary vein compliance parameter.

3. The method of claim 1, wherein the signal comprises at least one of a pressure or a volume of flow through the tissue from at least one of ex vivo lung perfusion and a bioreactor.

4. The method of claim 1, further comprising determining, by the one or more processors, at least one of the airway component, the vascular component, or the barrier component based at least in part on comparing the signal with native lung tissue data.

5. The method of claim 1, wherein the leak comprises at least one of a proximal vascular leak or a distal vascular leak based on at least one of the vascular component or the barrier component.

6. The method of claim 1, wherein the signal is received from a perfusion device that applies fluid flow to the tissue, the method further comprising adjusting, by the one or more processors, operation of the perfusion device responsive to the at least one of the integrity, the leak, or the patency.

7. The method of claim 1, wherein the tissue is the engineered tissue, and the signal is received responsive to applying fluid flow to the tissue, the method further comprising controlling, by the one or more processors, generation of the tissue responsive to the at least one of the integrity, the leak, or the patency.

8. The method of claim 1, wherein the tissue is the engineered tissue, and the signal is received responsive to applying fluid flow to the tissue, the method further comprising controlling a culture time of generation of the tissue responsive to the at least one of the integrity, the leak, or the patency.

9. The method of claim 1, further comprising determining, by the one or more processors, an ex vivo lung perfusion metric using the model.

10. A system, comprising:

one or more processors configured to:

receive a signal indicative of at least one of a flow or a pressure through a tissue, the tissue comprising at least one of a tissue scaffold, an engineered tissue, or a native tissue;

apply the signal as an input to a model comprising an airway component corresponding to an airway of the tissue, a vascular component corresponding to at least one of an artery or a vein of the tissue, and a barrier component between the airway component and the vascular component; and generate, responsive to applying the signal to the model, at least one of an integrity of an airway barrier corresponding to the barrier component, a leak of the tissue, or a patency of one or more vessels of the tissue.

11. The system of claim 10, further comprising a perfusion device configured to apply fluid flow to the tissue and detect the signal.

12. The system of claim 11, wherein the one or more processors are configured to control operation of the perfusion device responsive to the at least one of the integrity, the leak, or the patency.

13. The system of claim 10, further comprising a bioreactor configured to generate the tissue as an engineered tissue, wherein the one or more processors are configured to control operation of the bioreactor responsive to the at least one of the integrity, the leak, or the patency.

14. The system of claim 13, wherein the one or more processors are configured to control a culture time of generation of the tissue responsive to the at least one of the integrity, the leak, or the patency.

15. The system of claim 10, wherein the airway component comprises an airway resistance parameter and an airway compliance parameter, the barrier component comprises a barrier resistance parameter and a barrier compliance parameter, and the vascular component comprises a pulmonary artery resistance parameter, a pulmonary vein resistance parameter, and a pulmonary vein compliance parameter.

* * * * *